United States Patent [19]

Havera et al.

[11] Patent Number: 4,853,329

[45] Date of Patent: Aug. 1, 1989

[54] STABILIZATION OF MICROBIAL RENNET

[75] Inventors: Herbert J. Havera, Edwardsburg, Mich.; John D. Humphreys, Elkhart; Joan M. Jazdzewski, South Bend, both of Ind.

[73] Assignee: Miles Inc., Elkhart, Ind.

[21] Appl. No.: 214,027

[22] Filed: Jun. 27, 1988

[51] Int. Cl.$^4$ .............................................. G09B 17/00
[52] U.S. Cl. ...................................... 435/183; 435/184
[58] Field of Search ................................. 435/183, 184

[56] References Cited

U.S. PATENT DOCUMENTS 4,255,454 3/1981 Branner ............................. 435/184
4,591,565 5/1986 Branner ............................. 435/184

Primary Examiner—Peter D. Rosenberg
Attorney, Agent, or Firm—Jerome L. Jeffers

[57] ABSTRACT

Microbial rennet from *Rhizomucor pusillus* which has been oxidized to increase its thermal lability has a normal pH of about 5.5 in aqueous solution. It has been discovered that the stability of such solutions can be increased by raising the pH to a level of from 6.0 to about 8.5.

10 Claims, No Drawings

STABILIZATION OF MICROBIAL RENNET

BACKGROUND OF THE INVENTION

Calf rennet, obtained from the fourth stomach of unweaned calves, has traditionally been used as the coagulant for milk in the production of cheese. More recently an enzyme producing during the fermentation of certain fungi has been found to be a suitable replacement for calf rennet, the supply of which is limited by the availability of calf stomachs.

While the milk clotting enzyme from fungi (typically referred to as microbial rennet) is quite suitable for making cheese, it has a higher degree of thermal stability than calf rennet, which property is disadvantageous because the rennet ends up in the whey during the cheese making process resulting in proteolosis of the whey protein. Calf rennet does not present this problem because it is deactivated at ordinary pasturization temperatures. Cornelius reports in U.S. Pat. No. 4,348,482 that the thermal stability of microbial rennet can be decreased without substantially reducing its milk clotting activity by contacting an aqueous solution thereof with a methionine-oxidizing agent. This process, has achieved significant acceptance in the marketplace, especially with rennet from the species Rhizomucor miehei (formerly *Mucor miehei*). The taxonomy of the genus Mucor was revised and both *Mucor pusillus* and *Mucor miehei* were reclassified into a new genus Rhizomucor because they were determined to be sufficiently different from other members of the genus Mucor to justify such reclassification.

Cornelius also reports in U.S. Pat. No. 4,362,818 that the milk coagulating activity of the microbial enzyme obtained from *R. pusillus* can be increased by acylating the enzyme with selected acid anhydrides, including maleic anhydride. This acylation typically results in an increase of about 50% in the enzyme's activity.

Higashi et al report in U.S. Pat. No. 4,530,906 that the coagulating activity of microbial rennet from *R. pusillus* can be increased by treating it with succinic anhydride and have reported a low proteolytic activity/milk coagulating activity for the treated enzyme. They also report the method of improving microbial rennet from *Mucor pusillus* by acylating with a dicarboxylic acid anhydride and then oxidizing with an oxidizing agent.

The *R. pusillus* rennet which has been treated in the manner described above has obvious advantages as compared to the untreated material. However, it has been observed that its stability in aqueous solution is less than that of the untreated material. For example studies have indicated that the treated material lost 30% of its activity after 3 months at 40° C. and pH 5.3 whereas the untreated material lost only 5% activity. Stabilization of modified rennet from *R. pusillus* is desirable because such extensive loses of activity which occur even under refrigerated conditions, are unacceptable to cheese manufacturers since lost enzyme activity means increased cost and also increases uncertainty over the quantity of coagulant to add to the cheese milk to obtain a satisfactory set time. A considerable body of literature exists on the topic of enzyme stabilization and has been reviewed by Schwimmer in Source Book of Food Enzymology, AVI Publishing Company, Inc. Pp. 101–103, but there is little literature on the stabilization of rennet solutions because these enzymes are sufficiently stable (unmodified) under typical formulation conditions: 15–20% NaCl, 2% Na propionate, 0.5% Na benzoate, pH 5.0–5.5. Solutions of modified rennet from *R. pusillus* typically have a natural pH in the range of 5.0 to 5.5 which is the pH they stabilize at when the enzyme powder is dissolved in water. The *R. miehei* rennet solutions typically have an even lower pH (<pH 4.5) which is probably the pH that exists in the solution after the recovery process for the enzyme is completed. The native enzymes are relatively stable under these conditions, the stability problem only becoming apparent when dealing with the thermolabile (oxidized) rennet.

In practice, the alteration of the rennet solution's pH is straightforward. To a rennet solution, optionally containing sodium chloride (15–20% w/v) and other antimicrobial preservatives, such as sodium benzoate or sodium propionate, there is slowly added, with efficient stirring, a solution of an appropriate base (approximately 1M is a convenient concentration) until the desired pH level is reached. A weak base such as ammonium hydroxide is preferred since it will not cause localized increases in the pH which may tend to inactivate some of the enzyme. For this reason, strong bases such as alkali metal hydroxides, if used at all, should be very carefully added to the rennet solution. In addition, the inactivation of enzyme will be minimized if the base is added thereto slowly at room temperature or lower to thereby ensure dissipation of heat generated during the neutralization reaction.

The method of practicing the present invention and the results achieved thereby are further illustrated by the following examples:

EXAMPLE I

Solutions of oxidized and oxidized maleylated *R. pusillus* rennet were adjusted to various pH's between 5.5 and 8.5 by the careful addition of 1M sodium hydroxide. The samples were incubated at 37° C. in screw-cap test tubes for ten days. After this time milk-clotting activity was determined and compared with that of a zero time sample. Milk-clotting activity was determined on a solution of non-fat powdered milk (10.5% w/v) containing calcium chloride (0.02% w/v) at 32° C. Activity (in Rennet Units/ml) is calculated by comparing the clotting time of the test sample with that of a standard of known clotting activity (50 RU/ml). The results of this experiment are set out in Table I.

TABLE I

| Effect of pH on Stability of Oxidized and Oxidized/Maleylated *R. pusillus* rennets | | | | |
|---|---|---|---|---|
| | Original pH | (0 Time) | RU/ml (10 Days) | Loss (%) |
| Oxidized rennet | 5.5 | 148.6 | 94.3 | 36.5 |
| | 6.0 | 141.9 | 102.9 | 27.5 |
| | 6.5 | 143.3 | 120.4 | 15.9 |
| | 7.0 | 140.8 | 130.4 | 7.5 |
| | 7.5 | 138.9 | 126.2 | 8.9 |
| | 8.0 | 141.5 | 120.5 | 14.8 |
| | 8.5 | 142.2 | 114.9 | 19.2 |
| Oxidized/Maleylated rennet | 5.5 | 280.2 | 191.8 | 31.5 |
| | 6.0 | 266.1 | 207.1 | 22.1 |
| | 6.5 | 256.9 | 219.6 | 14.5 |
| | 7.0 | 246.3 | 222.6 | 9.6 |
| | 7.5 | 235.5 | 210.6 | 10.6 |
| | 8.0 | 236.3 | 207.5 | 12.2 |
| | 8.5 | 231.1 | 182.7 | 20.9 |

From the data of Table I it can be determined that the rennet solutions are maximally stable at a pH of around 7.0.

EXAMPLE II

A long term stability study was initiated at 4° C. to confirm the results of the accelerated study shown in Example I. A solution of oxidized *R. pusillus* rennet was adjusted to various pH's between 5.5 and 8.0 and incubated in screw-cap test tubes at 4° C. for four weeks. Samples were assayed for milk-clotting activity at weekly intervals. A control sample (pH not adjusted) was also included. The results of this experiment are set out in Table II.

TABLE II

Stability of Oxidized *R. pusillus* Rennet at Various pH's at 4° C.

| Initial pH | (RU/ml) and Loss (%) after | | | | |
|---|---|---|---|---|---|
| | 0 Weeks | 1 Weeks | 2 Weeks | 3 Weeks | 4 Weeks |
| 5.43 (control) | 163 | 152 (6.9) | 153 (6.2) | 145 (10.9) | 136 (16.7) |
| 5.5 | 165 | 151 (8.4) | 153 (7.4) | 144 (12.6) | 131 (20.3) |
| 6.0 | 155 | 151 (2.5) | 159 (0) | 153 (1.3) | 153 (1.3) |
| 6.5 | 153 | 148 (2.9) | 151 (1.2) | 153 (0) | 154 (0) |
| 7.0 | 150 | 147 (1.8) | 156 (0) | 148 (1.5) | 148 (1.7) |
| 7.5 | 142 | 145 (0) | 154 (0) | 144 (0) | 142 (0) |
| 8.0 | 140 | 140 (0) | 149 (0) | 138 (1.3) | 132 (5.9) |

From the data of Table II, it can be determined that the rennet solution is most stable in the pH range 6.0–80.

What is claimed is:

1. An aqueous solution of microbial rennet which has been derived from an organism of the species *Rhizomucor pusillus* and oxidized to increase its thermal lability having a pH within the range of from 6.0 to 8.5 which rennet solution exhibits greater storage stability than do such solutions whose pH is below 6.0.

2. The solution of claim 1 wherein the pH is within the range of from 6.5 to 7.5.

3. The solution of claim 1 wherein the pH is within the range of 6.9 to 7.1.

4. A method of increasing the stability of oxidized microbial rennet from *Rhizomucor pusillus* in aqueous solution which comprises raising the pH of such aqueous solution to a level within the range of 6.0 to 8.5.

5. The method of claim 4 wherein the pH is raised to a level of from 6.5 to 7.5.

6. The method of claim 4 wherein the pH is raised to a level within the range of 6.9 to 7.1.

7. The method of claim 4 wherein a weak base is used to raise the pH.

8. The method of claim 7 wherein the base is ammonium hydroxide.

9. The method of claim 4 wherein the rennin has been acylated to increase its milk clotting activity in addition to its having been oxidized.

10. An aqueous solution of microbial rennet derived from *Rhizomucor pusillus* which has been oxidized to increase its thermal lability and which has been acylated to increase its milk clotting activity, such solution being characterized by having a pH of from 6.0 to 8.5 and exhibiting greater storage stability than do such solutions whose pH is less than 6.0.

* * * * *